United States Patent [19]

Barberet et al.

[11] Patent Number: Plant 6,057

[45] Date of Patent: Dec. 8, 1987

[54] CARNATION NAMED LONPACHEL

[75] Inventors: Nicole Barberet; Yves Ducloux, both of Antibes, France

[73] Assignee: Laboratoire de Physiologie Vegetale de la Londe, La Londe, France

[21] Appl. No.: 811,993

[22] Filed: Dec. 23, 1985

[30] Foreign Application Priority Data

Mar. 14, 1985 [FR] France ..... 5145

[51] Int. Cl.[4] ..... A01H 5/00

[52] U.S. Cl. ..... Plt./71

[58] Field of Search ..... Plt./71

*Primary Examiner*—Robert E. Bagwill

*Attorney, Agent, or Firm*—Charles W. Rummler; John B. Lungmus

[57] ABSTRACT

A new variety of carnation plant particularly distinguished by the very light pink coloring of its medium sized blooms which are borne singly on long, strong stems; the plant being further distinguished by its profuse and recurrent production of blooms in spring, mid-season and fall, its vigorous and upright growth to a medium height and its resistance to *Fusarium oxysporum.*

1 Drawing Figure

BACKGROUND OF THE NEW PLANT

This new carnation cultivar originated as a seedling at La Londe, Les-Maures, Var., France, resulting from our crossing of selected varieties of plants in our collection of various varieties maintained for breeding purposes, the object of the crossing being to produce a plant having very good quality of flower stem and plant, and having a bloom coloration in the pink range. This seedling was selected for propagation because it appeared to fulfill our objectives and this selected seedling was propagated by means of cuttings at La Londe. Propagation was continued through several generations by both cuttings and In Vitro propagation and this has demonstrated that the new plant has retained all of the distinguishing characteristics of the original seedling, that these characteristics hold true from generation to generation, and appear to be firmly fixed.

DESCRIPTION OF THE DRAWING

Our new carnation cultivar is illustrated by the accompanying photographic drawing, which shows a group of flowers in various stages of maturity ranging from a newly opened bud to a fully opened bloom, the color rendition being as nearly true as it is reasonably possible to obtain from conventional photographic procedures.

DESCRIPTION OF THE NEW PLANT

The following is a detailed description of our new carnation cultivar based upon observation of plants grown in southern France during the current year, the color designations being according to The R.H.S. Colour Chart published by The Royal Horticultural Society of London, England.

THE PLANT

Origin: Seedling.

Parentage:

*Seed parent.*—Stock variety 76 P 11 (unnamed and unpatented).

*Pollen parent.*—Stock variety 92 88 OR (unnamed and unpatented). These plants are maintained in our collection for breeding purposes and their identities are fully recorded at our breeding facilities at La Londe.

Classification:

*Botanic.*—*Dianthus caryophyllus.*

*Commercial.*—Standard carnation.

Form: Bush, with at least four stems emitted near the ground.

Height: About 93 cm., in average, at eight months of growth.

Main stem length: Less than 15 cm. owing to pinching.

Growth: Vigorous and upright.

Strength: Rigid.

Branching character: Branches are few.

Foliage:

*Quantity.*—Moderately abundant.

*Number of leaves.*—More than 120.

*Leaf size.*—About 16.2 cm. long and 1.1 cm. in width.

*Leaf shape.*—Linear, at the seventh node, with curved margins and acuminate apex.

*Texture.*—Leathery

*Color.*—Upper side — RHS 189A. Under side — RHS 189A.

*Ribs and veins.*—Barely noticeable.

*Rachis.*—Barely noticeable.

THE BUD

Size: Medium.

*Diameter.*—About 2.1 cm.

*Length.*—About 2.6 cm.

Form: Ovoid.

Rate of opening: Normal.

Color of petals: When sepals first divide and petals begin to unfurl, RHS 49D.

Sepals:

*Number.*—Five.

*Character.*—Joined together at the calyx and sharp pointed at the apex. The sepals are hooded over the bud until it begins to break and when the flowers open the sepals stand up.

*Color.*—Inside — RHS 145D. Outside — RHS 139C and RHS 143A.

*Striae.*—The Striae are longitudinal.

Calyx:

*Shape.*—Funnel shaped.

*Size.*—Medium large and of medium breadth and length.

*Splitting.*—The calyx very rarely splits.

*Aspect.*—Smooth.

Flower stem:

*Length.*—About 70 cm.

*Character.*—Erect and rigid.

*Color.*—RHS 89A.

THE FLOWER

Blooming habit: Recurrent and profuse, blooming in spring, midseason and the fall with a tendency to fewer blooms during fall.

Size of bloom: Medium.

*Diameter.*—About 8.5 cm.

*Depth.*—About 6 cm. in average.

Borne: Singly on rigid, upright stems.

Shape: Flat when bloom first opens and becoming dome-shaped as the bloom matures.

Petalage:

*Number of petals.*—About 62, in average.

*Arrangement.*—Imbricated.

*Form.*—Fan-shaped with rounded margins and finely serrated outer end edges.

*Texture.*—Leathery.

*Appearance.*—Satiny.

*Color.*—Outer petals: Upper side: Body — RHS 49D. Base — Whitish. Reverse side — RHS 49D. Inside petals: Upper side: Body — RHS 49C with RHS 49D at the petal edges. Base — Whitish. Reverse side — RHS 49D.

Petaloids:

*Number.*—Less than 10.

*Size.*—Smaller than petals.

*Color.*—RHS 49D.

Flower stem:

*Length.*—About 70 cm.

*Color.*—RHS 189A.

*Character.*—Cut at tenth node, of good strength and upright.

Fragrance: Slight.

Persistence: The flower petals hang on and dry.

Disease resistance: Resistant to *Fusarium oxysporum* as observed INRA-Antibes-Alpes-Maritimes-France.

Lasting quality:

*As a cut flower.*—At least ten days in vase keeping.

REPRODUCTIVE ORGANS

Stamens:

*Number.*—11 to 17 arranged around the ovary.

Anthers:

*Size.*—Less than 4 mm.

Filaments:

*Length.*—About 2.6 cm.

*Color.*—Whitish.

Pistils:

*Number.*—3 or 4.

Styles:

*Length.*—About 2.8 cm.

*Color.*—Whitish.

Stigmas:

*Color.*—Whitish and lightly pink.

Ovaries: Ovary is ribbed.

The general characteristics of this plant can be more-or-less strongly modulated under the influence of environmental conditions and method of cultivation. In general, this new plant is similar to "Barlo II" (U.S. Plant Pat. No. 3,406), has less serration of petals, the calyx does not split and this plant is resistant to *Fusarium oxysporum.*

We claim:

1. A new and distinct carnation cultivar, substantially as herein shown and described, characterized by the very light pink coloration of its medium sized flowers which are borne singly on sturdy, upright and rigid flower stems.

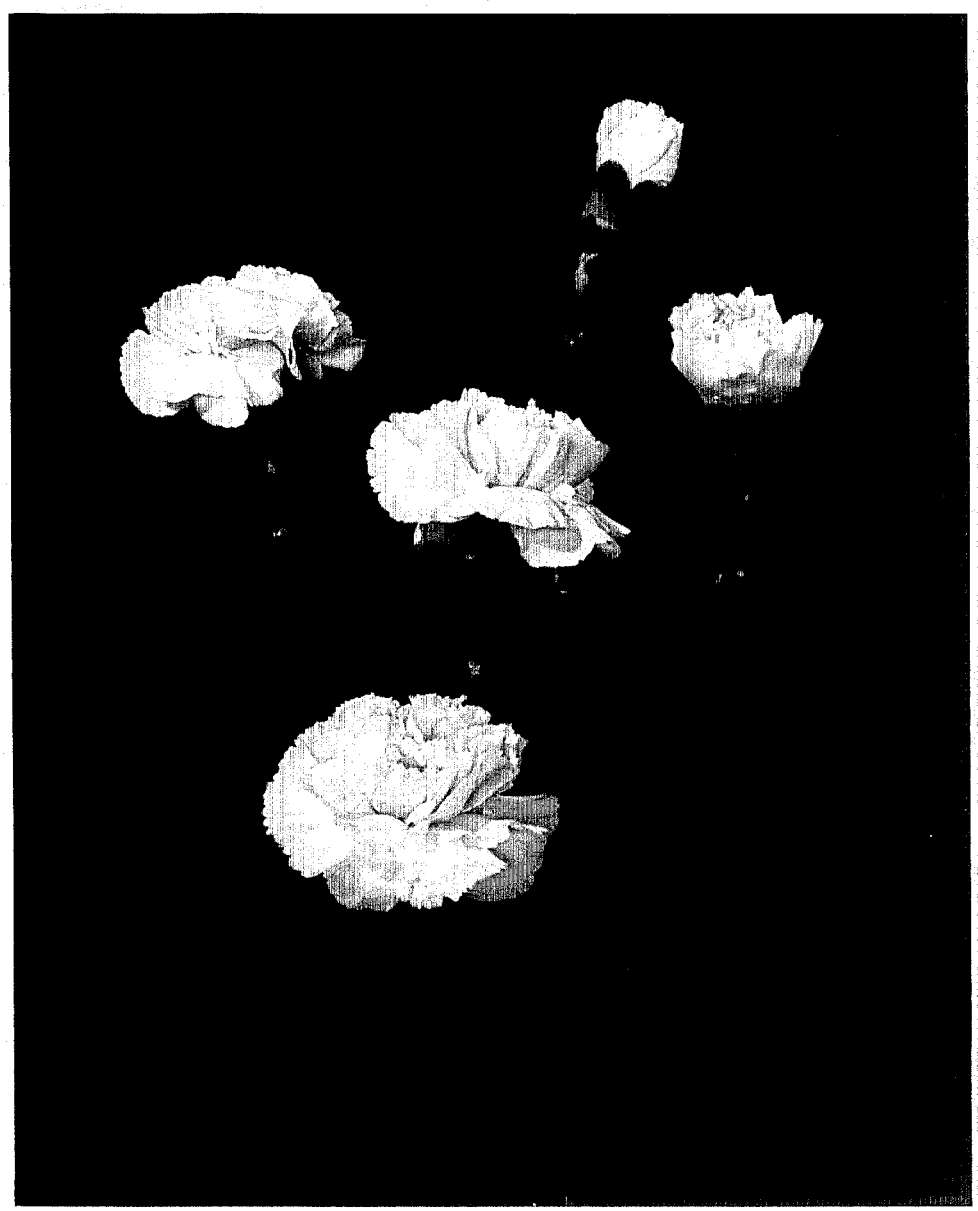

* * * * *